(12) United States Patent
Saukonoja et al.

(10) Patent No.: US 10,130,896 B2
(45) Date of Patent: Nov. 20, 2018

(54) PROCESS FOR PURIFYING HYDROCARBONS

(71) Applicant: BOREALIS AG, Vienna (AT)

(72) Inventors: Jouni Saukonoja, Porvoo (FI); Tero Lindholm, Porvoo (FI); Tero Pakala, Porvoo (FI); Timo Pakala, Porvoo (FI)

(73) Assignee: Borealis AG, Vienna (AT)

( * ) Notice: Subject to any disclaimer, the term of this patent is extended or adjusted under 35 U.S.C. 154(b) by 0 days.

(21) Appl. No.: 14/770,649

(22) PCT Filed: Feb. 26, 2014

(86) PCT No.: PCT/EP2014/053742
§ 371 (c)(1),
(2) Date: Aug. 26, 2015

(87) PCT Pub. No.: WO2014/131800
PCT Pub. Date: Sep. 4, 2014

(65) Prior Publication Data
US 2016/0008735 A1    Jan. 14, 2016

(30) Foreign Application Priority Data

Feb. 26, 2013 (EP) ..................... 13156818

(51) Int. Cl.
| | | |
|---|---|---|
| *C07C 37/68* | (2006.01) | |
| *B01D 3/14* | (2006.01) | |
| *C07C 37/08* | (2006.01) | |
| *C07C 45/80* | (2006.01) | |
| *C07C 45/82* | (2006.01) | |
| *C07C 7/10* | (2006.01) | |
| *B01D 11/04* | (2006.01) | |
| *C07C 7/04* | (2006.01) | |

(52) U.S. Cl.
CPC .......... *B01D 3/143* (2013.01); *B01D 11/0488* (2013.01); *B01D 11/0492* (2013.01); *C07C 7/04* (2013.01); *C07C 7/10* (2013.01); *C07C 37/08* (2013.01); *C07C 45/80* (2013.01); *C07C 45/82* (2013.01)

(58) Field of Classification Search
None
See application file for complete search history.

(56) References Cited

U.S. PATENT DOCUMENTS

| | | |
|---|---|---|
| 3,931,339 A | 1/1976 | Cooke |
| 5,120,902 A | 6/1992 | Tagamolila et al. |
| 5,220,103 A | 6/1993 | Tagamolila et al. |
| 6,066,767 A | 5/2000 | Zakoshansky et al. |

FOREIGN PATENT DOCUMENTS

| | | |
|---|---|---|
| GB | 743004 | 1/1956 |
| WO | 2004/046039 | 6/2004 |
| WO | 2009/080341 | 7/2009 |
| WO | 2010/069586 | 6/2010 |

OTHER PUBLICATIONS

International Search Report, dated Apr. 30, 2014, received in connection with International Patent Application No. PCT/EP2014/053742.
International Preliminary Report on Patentability, dated Sep. 1, 2015, received in connection with International Patent Application No. PCT/EP2014/053742.

*Primary Examiner* — Ana Z Muresan
(74) *Attorney, Agent, or Firm* — Meunier Carlin & Curfman LLC

(57) ABSTRACT

A process for washing hydrocarbons said process comprising: (I) distilling a crude acetone mixture preferably obtained from the cleavage of cumene hydroperoxide and containing hydrocarbons and water so as to form a bottoms fraction containing said hydrocarbons in an organic phase and an aqueous phase; (II) contacting at least a part of said bottoms fraction with an aqueous metal hydroxide solution so as to provide a concentration of 0.1 to 5 wt % MOH, where M is an alkali metal, in the aqueous phase; (III) separating the aqueous phase and the organic phase; (IV) contacting at least a part the organic phase from step (III) with an aqueous metal hydroxide solution so as to provide a concentration of 6 to 20 wt % MOH in the aqueous phase; (V) separating the organic phase and aqueous phase formed in step (IV); (VI) washing at least a part of the organic phase of step (V) with water.

13 Claims, 3 Drawing Sheets ively. The invention further provides an apparatus adapted to carry out the process of the invention.

PROCESS FOR PURIFYING HYDROCARBONS

This invention relates to an improved process for purifying hydrocarbons during the manufacture of phenol and acetone from cumene. In particular, the invention relates to a new process for washing the bottoms fraction from the acetone distillation column in the cumene process and ways of maximising process efficiency through the use of recycles of purge streams and the reuse of water. The resulting process is more efficient than that of the prior art as we maximise raw material utilisation. The invention further provides an apparatus adapted to carry out the process of the invention.

BACKGROUND

Phenol is commonly manufactured from cumene, wherein cumene is oxidized to cumene hydroperoxide (CHP) and the resulting oxidation product mixture is concentrated and subjected to a cleavage reaction. Subsequently, the cleavage product mixture is conducted to a distillation section, wherein the main products of the cleavage reaction, i.e. phenol and acetone, are first separated and then purified through a series of distillation or other purification steps. This is the cumene process.

The cleavage of cumene hydroperoxide to phenol and acetone is often catalysed using an acid meaning that the resulting cleavage product mixture contains not only acid catalyst residues but organic acid salts which interfere with the subsequent separation and purification of phenol and acetone. The organic acids may include, for example, formic acid and benzoic acid. Before the distillation of the main products of the cleavage reaction (i.e. phenol and acetone), these acids have to be neutralized to prevent, for example, side reactions and/or equipment corrosion during the distillation process.

Neutralization may be accomplished by treating the acids with a basic material, such as an aqueous alkaline agent, typically NaOH (caustic). During the neutralization reaction, salts are formed. However, these too can cause problems during the subsequent purification and recovery of phenol and acetone by distillation. For example, salt carryover to the distillation section causes fouling and down time, and thus capacity reduction.

The neutralization of the cleavage product mixture produced in a phenol production process has generally been conducted by adding a caustic agent to the mixture or by adding an aqueous salt solution optionally containing excess caustic agent, as in U.S. Pat. No. 6,066,767. This publication concerns a method for purifying CHP cleavage products in a purification process system. Purification is performed by extracting hydroxy acetone and carbonyl compounds with a water-salt solution at the neutralization stage by adding a caustic agent.

U.S. Pat. No. 3,931,339 concerns a process for the removal and neutralization of an acid catalyst and organic acid by-products from the reaction mixture resulting from cumene hydroperoxide cleavage. The process comprises extracting the acids from the organic phase into an aqueous phase and neutralizing them using an aqueous solution of an acidic or neutral inorganic salt, and an excess of alkali metal hydroxide or alkali metal phenate, separating the aqueous phase containing the neutralized acids from the mixture, then contacting the organic phase with an aqueous solution of an acidic or neutral inorganic salt and a weak acid, and thereafter again separating the aqueous phase from the mixture.

GB 743,004 concerns a process for the production of phenol and acetone from CHP, in which the acid and acidic organic impurities in the cleavage mixture are neutralized using an alkaline material. Corresponding salts of the acid and acidic impurities are then partly precipitated in the effluent, whereby they are removed by adding water to the neutralized cleavage mixture in an amount sufficient to cause formation of two phases. The aqueous phase will then contain substantially all of the salts. The salt content of the organic phase will, according to the publication, be less than 0.03% by weight, often as low as about 0.01% by weight.

Neutralisation of the cleavage product is thus usually carried out using fresh caustic solution and that can lead to high levels of caustic use. Also, when only fresh caustic is used in cleavage product neutralisation, the consequences are following:

1) The amount of wastewater from the plant is increased as so much is used to dilute the caustic down to appropriate concentration for neutralisation;
2) Sulphuric acid consumption is increased as the wastewater has to be neutralised (with sulphuric acid) before the de-phenolation step;
3) The steam consumption in the de-phenolation is increased (the more wastewater the more steam is required for de-phenolation step).

The neutralisation of the cleavage product from acid catalysed cleavage is not however, the only use of caustic in the phenol product process. In U.S. Pat. No. 5,220,103 and U.S. Pat. No. 5,120,902, caustic is used to wash recycled cumene. In WO2009/080341 and WO2010/069586, caustic is used to wash oxygen gas used for the oxidation reaction.

Caustic is also used, however, as a washing solution during hydrocarbon recovery, in particular during the recovery of the bottoms fraction from acetone distillation.

Once the cumene hydroperoxide has been cleaved to form phenol and acetone and once the reaction products have been neutralised, the phenol and acetone are separated by distillation and sent to separate parts of the plant for further purification. The acetone fraction, containing various impurities, is sent to a column for further purification as the acetone at this stage in the process is still intimately mixed with impurities such as water, unreacted cumene, organic acid salts, some sodium hydroxide and some residual phenol. These impurities must be removed from the acetone before it can be commercialised. Also, phenol and cumene are valued resources and are preferably recycled/isolated from the acetone fraction.

The present inventors have made a series of innovations to improve the production process here. Firstly, it has been surprisingly found that the hydrocarbon wash step (i.e. the washing of the bottoms from the acetone distillation column) is improved if two different concentrations of caustic are used in separate steps. In particularly a lower then higher concentration caustic solution should be employed. It is further noted that improvements can then be achieved if the twice washed hydrocarbons are washed once more with water. For process efficiency the water used in the washing step can be extracted from the washing step and used to dilute the caustic which is used for the second washing step. Caustic is typically supplied industrially at 50 wt % strength which is too high (and too expensive) for use industrially.

Moreover, the caustic used in the second washing step can be further diluted with water to act as the caustic for the first washing step. That water can again be derived from the third washing step or may simply be present in the bottoms fraction inherently.

As a final advantage, the concentration of caustic used in the first washing step is also at an ideal level for use in the neutralisation step which takes place after the cumene hydroperoxide cleavage reaction. The use therefore of a recycle of the first caustic wash from acetone bottoms washing to the neutralisation step forms a still yet further aspect of the invention. It has been surprisingly found, that instead of using only fresh caustic for that neutralisation, caustic from the hydrocarbons wash can be used to replace part or all of the fresh caustic typically used. That has major advantages in terms of raw material costs.

The present inventors have therefore devised an improved process which maximises the use of raw materials such as water and caustic, which on the scale used in industrial plants offers major economic benefits.

SUMMARY OF INVENTION

Thus viewed from one aspect the invention provides a process, e.g. for washing/purifying hydrocarbons said process comprising:

(I) distilling a crude acetone mixture preferably obtained from the cleavage of cumene hydroperoxide and containing hydrocarbons and water so as to form a bottoms fraction containing said hydrocarbons in an organic phase and an aqueous phase;

(II) contacting at least a part of said bottoms fraction with an aqueous metal hydroxide solution so as to provide a concentration of 0.1 to 5 wt % MOH, where M is an alkali metal, in the aqueous phase;

(III) separating the aqueous phase and the organic phase;

(IV) contacting at least a part the organic phase from step (III) with an aqueous metal hydroxide solution so as to provide a concentration of 6 to 20 wt % MOH, where M is an alkali metal, in the aqueous phase;

(V) separating the organic phase and aqueous phase formed in step (IV);

(VI) washing at least a part of the organic phase of step (V) with water.

In a preferred embodiment at least a part of the aqueous phase formed after step (VI) is used to dilute hydroxide so as to form the MOH solution required in step (IV). In a preferred embodiment, at least a part of the aqueous phase formed after step (IV) is diluted with water to form the hydroxide added in step (II). In a preferred embodiment, at least a part of the aqueous phase formed after step (II) is used to neutralise the cleavage products of an acid catalysed cumene hydroperoxide reaction.

In a further preferred embodiment the bottoms fraction containing hydrocarbons formed after step (I) comprises the hydrocarbons cumene and AMS.

In a further preferred embodiment, at least a part of the aqueous phase formed after step (II) is used in dephenolation. Thus viewed from another aspect the invention provides a dephenolation process said process comprising:

(I) distilling a crude acetone mixture preferably obtained from the cleavage of cumene hydroperoxide and containing hydrocarbons and water so as to form a bottoms fraction containing said hydrocarbons in an organic phase and an aqueous phase;

(II) contacting at least a part of said bottoms fraction with an aqueous metal hydroxide solution so as to provide a concentration of 0.1 to 5 wt % MOH, where M is an alkali metal, in the aqueous phase;

(III) separating the aqueous phase and the organic phase;

(IV) transferring at least a part of the aqueous phase to de-phenolation where the metal phenolate contained in the aqueous phase is neutralized in order to convert the phenolate to phenol, e.g. with sulphuric acid, and then stripped with steam in order to remove phenol from the aqueous phase.

In a preferred embodiment, the invention provides a process, e.g. for washing/purifying hydrocarbons said process comprising:

(I) distilling a crude acetone mixture obtained from the cleavage of cumene hydroperoxide and containing hydrocarbons and water so as to form a bottoms fraction containing said hydrocarbons in an organic phase and an aqueous phase;

(II) contacting said bottoms fraction with an aqueous metal hydroxide solution so as to provide a concentration of 0.1 to 5 wt % MOH, where M is an alkali metal, in the aqueous phase;

(III) separating the aqueous phase and the organic phase;

(IV) contacting the organic phase from step (III) with an aqueous metal hydroxide solution having a concentration of 6 to 20 wt % MOH, where M is an alkali metal, in the aqueous phase;

(V) separating the organic phase and aqueous phase formed in step (IV);

(VI) washing the organic phase of step (V) with water.

Viewed from another aspect the invention provides an apparatus suitable for carrying out a process as hereinbefore defined comprising:

an acetone distillation column (1);

a conduit (6) for carrying the bottoms fraction from column (1) to a separation vessel (2) optionally containing horizontal baffles and separation plates;

a conduit (9) for adding NaOH into separation vessel (2);

a conduit (7) for carrying the organic phase from vessel (2) to separation vessel (3) optionally containing horizontal baffles and separation plates;

a conduit (10) for adding NaOH to separation vessel (3);

a conduit (8) for carrying organic phase from vessel (3) to separation vessel (4) optionally containing horizontal baffles and separation plates;

a conduit (12) for adding water to vessel (4);

a conduit (11) for carrying the at least a part of the aqueous phase from vessel (4) to dilute the NaOH added via conduit (10); optionally a a conduit (13) for carrying at least a part of the MOH containing aqueous phase from vessel (3) to be added to vessel (2) via conduit (9); and optionally a conduit (14) to carry at least a part of the aqueous phase from vessel (2) to neutralisation of the cleavage product from cumene hydroperoxide cleavage.

The apparatus can also be provided with a conduit to carry at least a part of the aqueous phase from vessel (2) to dephenolation.

DETAILED DESCRIPTION OF INVENTION

The invention covers a new procedure for washing/purifying a hydrocarbon stream from the acetone purification stage of the cumene process for the manufacture of phenol and acetone. The cumene process for making phenol is well known and involves conversion of cumene to cumene hydroperoxide and cleavage of that hydroperoxide into phenol and acetone.

Thus cumene hydroperoxide is cleaved into phenol and acetone in cleavage reactors. Acids such as sulphuric acid are used as catalyst in that process and in a cleavage wash step, that acid is neutralised typically with NaOH and the resulting salt is washed away. The cleavage wash product typically contains phenol, acetone, cumene, AMS and dissolved water.

Acetone and phenol are then separated and crude phenol containing some heavy phenolic tars and impurities is removed via a bottom fraction. The top product is taken for further distillation where part of the acetone is distilled and returned back to the cleavage reactors. This improves the operation of the cleavage reactors. NaOH is added to remove aldehyde impurities through an aldol condensation reaction in this step. The aldol reaction is catalysed by NaOH.

The remaining acetone, water, cumene and AMS and NaOH are taken out from the bottom of that column and fed to distillation column.

This is the crude acetone fraction according to the invention and is therefore sent to a distillation column. The crude acetone used in the process of the present invention is that obtained after cumene hydroperoxide cleavage, neutralisation and separation of the formed acetone and phenol via distillation.

The crude acetone fraction obtained after the steps described above typically contains various impurities including some hydrocarbons. The hydrocarbons washed in the process of the invention generally comprise at least cumene and alpha methyl styrene. Impurities in the crude acetone fraction may include water, unreacted cumene, AMS, sodium hydroxide, phenol and some organic acid salts formed from impurities present in the reaction mixture such as formic and acetic acid salts.

During this acetone distillation stage, the acetone is removed overhead. Impurities are concentrated in the bottoms fraction and it is this bottoms fraction that is washed according to the first step of the invention.

Whilst the invention will now be described with reference to the use of sodium hydroxide (caustic) as the base, it will be appreciated that other alkali metal hydroxide, such as KOH might also be used.

The washing of the bottoms fraction is the lower concentration caustic wash step. Whilst it is generally known to wash the bottoms fraction of the acetone distillation column with caustic at this stage, the process of the present invention is more sophisticated and ensures a better quality of product and maximises raw material resources.

The purpose of the washing step is to remove one or more, preferably all of, water, organic acids, phenol and sodium hydroxide from the bottoms fraction of the acetone column before the remaining organic fraction is taken to a further distillation stage. In the next distillation stage, any residual organic acids in the organic phase cause corrosion and sodium residues cause heat exchanger and distillation tray fouling. Also, phenol is unwanted in later process steps where it disturbs selectivity in reactors.

From the bottom of the acetone distillation column comes therefore a stream with typically water, cumene and alpha methyl styrene with low amounts of other impurities, such as NaOH, phenol and organic acids. The water content of the fraction to be washed at this stage of the invention may be 30 to 60 wt %, preferably 40 to 50 wt % such as 45% water. The cumene content of the fraction to be washed may be 30 to 60 wt %, such as 35 to 50 wt %, preferably 43% cumene. The alpha methyl styrene content (AMS) of the bottoms fraction may be 5 to 20 wt % such as 10 to 15 wt %, preferably 12% alpha methyl styrene. The contents of phenol, and sodium hydroxide as impurities may be less than 5 wt % but often more than 0.4 wt %. Organic acids which are present are typically present at levels of less than 0.4 wt %.

As there are both organic and aqueous phases in this bottoms fraction, it presents as two liquid phases which can be separated by decantation. Before separation however, NaOH is added to the bottoms fraction, typically before the material enters a separation vessel. This addition can take place at ambient pressure and temperature.

The amount of NaOH added is designed to create a concentration of 0.1 to 5 wt % in the aqueous phase of the bottoms fraction being washed, preferably 0.5 to 2 wt % concentration solution. Ideally, enough NaOH solution is added such that the aqueous phase is adjusted to around 1 wt % NaOH. It will be appreciated that some form of mixing apparatus can be used to ensure intimate mixing between NaOH solution and the bottoms fraction.

Note that the bottoms fraction contains so much water at this stage of the process that it is impractical and too expensive to target a high level of NaOH in the aqueous phase at this point of the process. Percentages of more than 5 wt % NaOH in the aqueous phase are not therefore favoured.

The amount of NaOH added can vary but typically the NaOH solution is added in a weight ratio of around 1:10 to 1:200 relative to the weight of the bottoms fraction, such as 1:50 to 1:150, e.g. 1:100. Thus if there is 16 tons of bottoms fraction, perhaps 130 kg of aq. NaOH solution is required depending on the concentration of NaOH present in the solution.

The actual concentration of NaOH solution added may also vary but may typically be around 15 wt % NaOH. The concentration used will depend on the water content in the bottoms fraction. In a preferred embodiment, the concentration of the NaOH solution added will be the same as the concentration of the NaOH solution withdrawn in the aqueous phase from vessel (3) during the step (V) process.

This washing step enables removal of organic acids such as formic acid and acetic acid from the organic phase and phenol from the organic phase as corresponding sodium salts. These salts partition into the aqueous phase along with the NaOH solution. We have surprisingly found that the use of low concentration NaOH solutions, such as up to 2 wt % NaOH in the aqueous phase is enough to remove most of the organic acids and phenol from the organic phase. Also, this level of NaOH allows proper phase separation to occur between organic and aqueous phases. Adding more NaOH is therefore not necessary and would result in extra costs.

At this point in the process, the aqueous and organic phases are separated. The organic phase is preferably transferred to a further separation vessel. The aqueous phase can be further treated. For example, the aqueous phase can be treated to recover phenol present in the aqueous phase as that is a valuable resource. Phenol exists as the phenolate in the aqueous phase at this point and to recover phenol, it is preferred to acidify the aqueous phase to regenerate phenol. That can be achieved with an acid such as sulphuric acid. Sulphuric acid is readily available as it is typically used as the acid catalyst in the CHP cleavage reaction. Once converted back to phenol, it can be recovered from the aqueous phase in a conventional manner e.g. by stripping with steam. This forms a further aspect of the invention.

In a preferred embodiment however, the aqueous phase is split at this point. One part of the aqueous phase is transferred to cleavage product neutralisation and the another part to dephenolation, where the pH of the solution is lowered as discussed above with an acid and sodium phenoxides consequently converted to phenol which is further recovered.

The neutralisation process is discussed further below. The relative amounts of each stream are not crucial. In one embodiment, however, weight ratios of each stream may be aqueous stream to cleavage neutralization 5-30 wt %, preferably 15 wt %, aqueous stream to dephenolation 70-95 wt %, preferably 85 wt %.

In general, enough aqueous phase is transferred to the neutralisation step in order to effect neutralisation. This obviously reduces the requirement for fresh caustic in the neutralisation step and represents a cost saving. Note that the presence of any residual impurities in the aqueous phase is not a problem for the neutralisation step as those impurities are eventually removed later on in the process.

The organic phase formed after the first NaOH wash is also further treated. It is preferably transferred to a further separation vessel. In the present invention, the organic phase is then subject to a second washing step with caustic although this time at much higher caustic concentration. As the organic phase is essentially free of water at this stage of the process it is much easier to contact the organic phase with high concentration of caustic.

Thus, the organic phase is preferably contacted with enough NaOH solution to form a 6 wt % or more solution of caustic in the aqueous phase of the process at this point, such as 6 to 20 wt % caustic solution in the aqueous phase, e.g. 10 to 17 wt % caustic solution. Ideally a 15 wt % NaOH solution is present in the aqueous phase. The amount of caustic solution added can vary but preferably there is enough to form a discernable water phase in the second separation vessel. For example, the second caustic wash may represent at least 20 wt % of the organic phase present, such as at least 50 wt %. In a preferred embodiment, the amount of caustic solution added has the same weight at the organic phase at this point in the process, i.e. the mixing ratio is about 1:1. There can also be an excess of aq NaOH solution added, e.g. up to a 1:2 wt ratio, organic to aqueous phase. This addition can take place at ambient pressure and temperature or the temperature can be slightly elevated, e.g. to 30 to 50° C.

The inventors have surprisingly found that there are still residues of phenol in the organic phase before this second caustic wash. In order to convert those phenol residues to phenolates and hence force them to partition to the aqueous phase, the inventors have determined that the use of high concentration NaOH solutions are ideal. In a preferred embodiment, a 10 wt % or more NaOH solution is used to ensure conversion of phenol present in the hydrocarbon waste into phenolate and hence partition to water. It will be appreciated that the NaOH concentration in the aqueous phase after the second washing step is essentially the same as the NaOH concentration in the washing solution as there is no other significant source of water or NaOH present.

With this higher level of NaOH, any remaining phenol is converted to sodium phenoxide and removed from the organic phase in the aqueous phase. Moreover, it is preferred if a small purge stream is taken from the aqueous phase at this point to supply the NaOH needed for the lower NaOH step previously described. This purge can be further diluted with water to ensure the appropriate water content for the first wash step. Moreover, that water can be taken from the aqueous phase of the next step of the process as discussed further below, if desired. Ideally, dilution takes place using the aqueous phase present in the bottoms fraction.

Correspondingly fresh NaOH can be fed to maintain the NaOH concentration at the higher level in the second wash process.

The second caustic wash can therefore be considered to involve a circulation system where NaOH is added into the separation vessel, separation occurs, the aqueous phase is removed and added back in to the vessel, meantime a small purge is taken to act as the NaOH solution for step (II) and fresh caustic added to maintain the NaOH concentration.

The organic phase after the second caustic wash step can then be further washed with water, e.g. in another separation vessel. The preferably phenol-free organic phase can be treated to remove the last few remaining ppm's of dissolved NaOH. This is preferably achieved using a water wash. The water used is preferably such that its Na concentration is less than 100 ppm. Any NaOH in the organic phase dissolves in the water leaving an organic phase containing hydrocarbon compounds only, mainly cumene and alpha methyl styrene. The water wash step can take place at ambient pressure and temperature or the temperature can be slightly elevated, e.g. to 30 to 50° C. Again, the amount of the aqueous phase which is needed might vary and is not critical. Typically, the water added represents at least 20 wt % of the organic phase, such as at least 50 wt %.

The aqueous phase that results from this washing step is also an ideal source of water for producing the higher concentration caustic added to the second step of the process. Caustic is often supplied commercially in higher concentration that we want to use in the second step, such as 50 wt % caustic solution or 25 wt % caustic solution. Dilution of this caustic with fresh water uses a large amount of water. If however a purge of the aqueous phase from step 3 of the process is taken for diluting the NaOH used in the "higher" concentration NaOH wash in step 2, then the water can be used twice. This purge also keeps the Na concentration of the wash circulation below 100 ppm. Without this purge, Na content in the water wash can build up.

The organic phase, now free of organic acids, phenol and sodium is taken further to distillation to separate the organics. That process is conventional and will not be further discussed herein. In general, the alpha methyl styrene is hydrogenated to form cumene and the cumene formed during hydrogenation as well as the cumene already present in the organic phase are combined and recycled to the start of the whole process (or to some other convenient part of the process).

The use of this final stage water wash is preferred as it allows the process to be even more efficient. With a water wash there should be no carry over of caustic into the organic phase. Any caustic can initiate fouling reactions such as polymerisation reactions when the organic phase is subsequently distilled to separate organic components.

There is also a risk that any residual NaOH can find its way back to the oxidation section of the plant. As noted above, the cumene present in the organic phase is recycled back to the start of the process. Also, the alpha methyl styrene present in the organic phase is hydrogenated to form cumene and also recycled. If any NaOH is present in the organic phase that can therefore travel back to the start of the process and hence into the oxidation reactors via the cumene recycle. That is not desirable as the caustic catalyses the cleavage of cumene hydroperoxide into phenol and acetone and the presence of phenol in the oxidation reactor slows down and perhaps even stops the oxidation reaction of cumene to CHP.

Again therefore the water wash step can involve a circulation as water is added to the separation vessel, separation occurs, water is removed and recycled back into the vessel with a purge taken to effect dilution of the second caustic wash (and possibly the first caustic wash) and fresh water added to maintain the water level.

As noted above, a part of the aqueous phase formed after the water wash can also be used to dilute the caustic solution required for the first caustic wash. This maximises water utilisation in the process of the invention. The caustic required for the first washing step is therefore preferably derived from the aqueous phase of the second wash optionally diluted with the aqueous phase of the water washing step.

As noted above, at least a part of the aqueous purge from the first caustic wash step containing low levels of caustic can be transferred to cleavage neutralisation reaction and used to neutralise the acid catalyst and acid residues formed during cumene hydroperoxide cleavage. In conventional operation, fresh caustic only is added to the cleavage product to cause neutralisation. By using a recycle stream, we use less caustic and maximise raw material resource. The neutralisation step is otherwise conventional.

Preferably, as mentioned above, the cleavage of cumene hydroperoxide into cleavage products (the main ones being phenol and acetone) occurs through an acid-catalyzed reaction making the cleavage product mixture acidic. The acid present in this acid-containing organic mixture is preferably an inorganic acid, and more preferably sulfuric acid. The concentration of added acid in the cleavage product mixture is about 0.005-0.2 wt. %, preferably 0.01-0.15 wt. %. The amount of NaOH required for neutralization is thus easy to calculate.

According to a preferred embodiment of the present invention, the added acids are neutralized by adjusting the pH of the mixture to about 4.5-6.5 using an aqueous caustic solution.

The temperature during the neutralization and the salt-removal of the present invention will generally be maintained at 30-50° C., preferably at about 40° C.

This invention therefore reduces the amount of fresh caustic used in the cumene process as the same NaOH can be used in the two washing steps and in neutralisation. We minimise water usage as the same water can be used for water washing, dilution of the first and second caustic solutions and ultimately also in the neutralisation step.

Due to the use of two different caustic solution concentrations in separate washing steps, we also reduce the amount of acid, such as sulphuric acid, required to recover phenol during de-phenolation. As the majority of the phenol is extracted into the aqueous phase during the first washing step, less acid is required to form phenol compared to the situation where a higher caustic solution concentration is used.

We also reduce the amount of water used and the amount of steam required in dephenolation. Because we recycle part of the caustic aqueous phase obtained after step (II) to product cleavage neutralisation, there is less aqueous phase to acidify to isolate phenol. We use less acid therefore. Also, with less phenol to recover, we use less steam stripping phenol from water.

These advantages lead to considerable savings in plant. Caustic consumption per ton produced phenol can be decreased. Acid, such as sulphuric acid consumption per ton produced phenol can be decreased. Steam consumption per ton produced phenol can be decreased. Water use per ton produced phenol can be decreased. We also minimise the amount of waste water produced.

The invention will now be described with reference to FIG. 1 to 3.

HYDROCARBON WASH PROCESS DESCRIPTION

Figure 1:
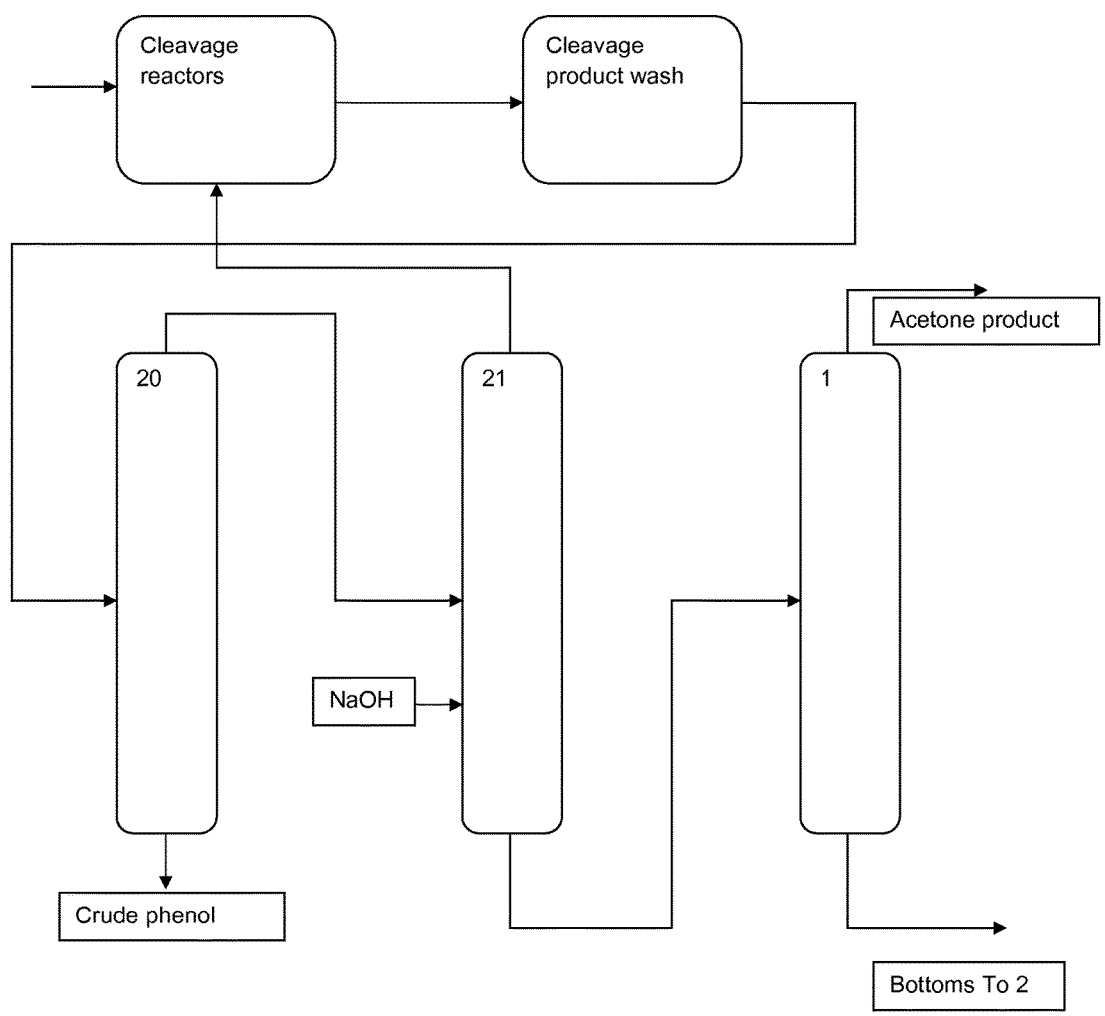
FIG. 1 shows a cumene hydroperoxide cleavage set up with subsequent phenol/acetone separation.

In FIG. 1, cumene hydroperoxide is cleaved into phenol and acetone in the cleavage reactors. Sulphuric acid is used as catalyst, and in the cleavage wash the acid is neutralised with NaOH and the resulting salt is washed away. The cleavage wash product contains phenol, acetone, cumene, AMS and dissolved water. In column 20, crude phenol containing some heavy phenolic tars and impurities is removed from the column bottom. The top product is taken to column 21, where part of the acetone is distilled and returned back to the cleavage reactors. This improves the operation of the cleavage reactors. The remaining acetone, water, cumene and AMS and taken out from the bottom of the column 21 and fed to column 1.

In column 21, some NaOH is added to remove aldehyde impurities through aldol condensation reaction (which is catalysed by NaOH). This NaOH goes with the bottom product to column 1.

Figure 2:
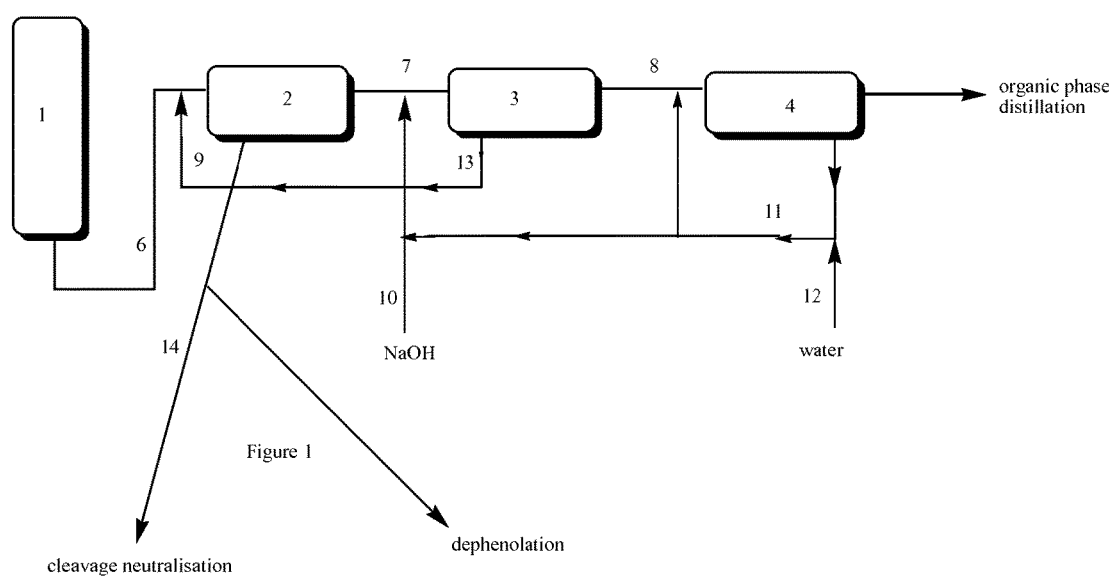
FIG. 2 shows an apparatus of use in the process of the invention.

In column 1, pure acetone is removed as distillate. Because acetone, a dissolving agent, is removed from the mixture, two liquid phases form in the bottom of the column. This two-phase stream is the "bottoms fraction" of step (I) of the claimed process and is taken to separation vessel 2 according to scheme in FIG. 2.

The purpose of the claimed process is to remove water, organics, phenol and sodium from the bottom product of crude acetone column 1 before it is taken to the next distillation stage. In the next distillation stage, organic acids cause corrosion and sodium causes heat exchanger and distillation tray fouling. Phenol is unwanted in later process steps where it disturbs selectivity in reactors.

From the bottom of the distillation 1 comes a stream with 45% water, 43% cumene and 12% AMS, in addition to some phenol, organic acids and sodium hydroxide as impurities. This stream has two liquid phases (organic and aqueous) which are separated by decantation in separation vessel 2. NaOH concentration of the aqueous phase is adjusted through addition of NaOH via conduit (9) to around 1 wt %. This is done to remove organic acids and phenol from the organic phase as corresponding sodium salts. These partition in the aqueous phase. 1 wt % NaOH is enough to remove most of the acids and phenol and to allow proper phase separation. Adding more NaOH is not necessary and would result in extra costs.

The water phase leaving separation vessel 2 via conduit (14) is split to two streams; one stream going to cleavage product neutralisation (not shown) and the other one to dephenolation (not shown), where the pH of the solution is lowered with acid and sodium phenoxides consequently converted to phenol which is further recovered, e.g. by steam stripping.

The organic phase from separation vessel 2 is taken to vessel 3, where it is contacted with a 15 wt % NaOH circulation. With 15% NaOH, remaining phenol in the organic phase is converted to sodium phenoxide and removed from the organic phase via partition into the aqueous phase. A small purge stream is taken from the 15% NaOH circulation to separation vessel 2 via conduit (9), in order to maintain the NaOH concentration there at 1 wt %.

Correspondingly, fresh NaOH is fed to vessel 3 via conduit (10) to maintain the NaOH concentration at 15 wt % in the circulation.

The phenol-free organic phase is then taken to vessel 4 where the few remaining ppm's of dissolved NaOH are removed with a water wash. The water wash is done with a water circulation having less than 100 ppm of Na in it. A purge of this water stream is taken for diluting 25 wt % NaOH into 15 wt % NaOH in conduit (10). This purge also keeps the Na concentration of the wash circulation below 100 ppm. The organic phase from vessel 4, now free of organic acids, phenol and sodium is taken further to distillation.

Table 1 summarises typical properties within vessels 2, 3 and 4.

| Unit | 2 | 3 | 4 |
|---|---|---|---|
| T/C | 40 | 40 | 40 |
| P/bar | 1 | 1 | 1 |
| Phase ratio aq./org. | 0.8 | 1.8 | 0.6 |

Figure 3:
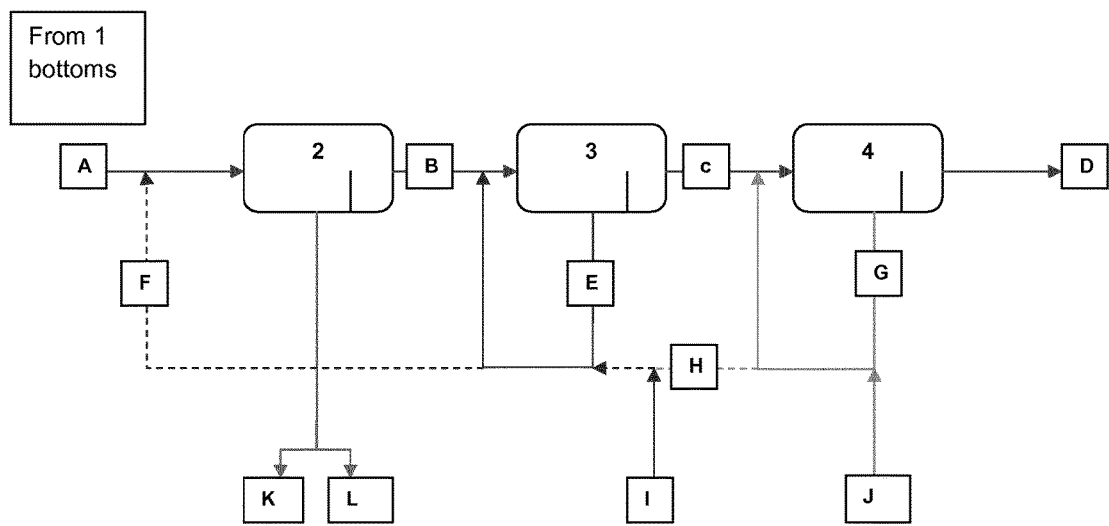
FIG. 3 shows flow rates possible in the FIG. 2 apparatus.

Table 2 summarises the nature of the material in each stage of the process and possible flows based on FIG. 3.

| | Flow | | | | | | | | | | | |
|---|---|---|---|---|---|---|---|---|---|---|---|---|
| | A | B | C | D | E | F | G | H | I | J | K | L |
| Phase | Org + Aq | Org | Org | Org | Aq | Aq | Aq | Aq | Aq | Aq | Aq | Aq |
| Flow kg/h | 16000 | 9000 | 9000 | 9000 | 16000 | 130 | 5000 | 75 | 125 | 200 | 1500 | 5500 |
| Org kg/h | 9000 | 9000 | 9000 | 9000 | | | | | | | | |
| Water kg/h | 7000 | | | | 16000 | 130 | 5000 | 75 | 125 | 200 | 1500 | 5500 |
| NaOH w-% | 0.4 | | | | 15 | 15 | | | 25 | | 1 | 1 |
| NaOH ppm | | ~100 | ~20 | 5 | | | 100 | 100 | | | | |

E is the flow of aqueous material leaving vessel. 3. F is flow of NaOH to vessel 2 G is the flow of aqueous phase leaving vessel 4. H is flow from G to dilute the NaOH entering at I. I is the flow of fresh NaOH. J is the flow of fresh water (12). K is flow to cleavage neutralisation and L to dephenolation.

The invention claimed is:

1. A process comprising:
   (I) distilling a crude acetone mixture containing hydrocarbons and water to form a bottoms fraction containing an organic phase and an aqueous phase, wherein the organic phase contains cumene and alpha methyl styrene; wherein the crude acetone mixture is obtained from the cleavage of cumene hydroperoxide;
   (II) contacting at least a part of said bottoms fraction with an aqueous metal hydroxide solution, thereby forming an organic phase and an aqueous phase, wherein the aqueous metal hydroxide solution provides a concentration of 0.1 to 5 wt % MOH, where M is an alkali metal, in the aqueous phase;
   (III) separating the aqueous phase and the organic phase from step (II);
   (IV) contacting at least a part the organic phase from step (III) with a second aqueous metal hydroxide solution, thereby forming an organic phase and a second aqueous phase, wherein the second aqueous metal hydroxide solution provides a concentration of 6 to 20 wt % MOH, where M is an alkali metal, in the second aqueous phase;
   (V) separating the organic phase and the second aqueous phase from step (IV); and
   (VI) washing at least a part of the organic phase from step (V) with water;
   wherein each of steps (II), (IV), and (VI) are carried out in separate vessels.

2. The process as claimed in claim 1, wherein MOH is NaOH.

3. The process as claimed in claim 1, wherein a third aqueous phase is formed in step (VI) and at least a part of the third aqueous phase is used to dilute hydroxide to form the MOH solution added in step (IV).

4. The process as claimed in claim 1, wherein at least a part of the second aqueous phase from step (IV) is diluted with water to form the hydroxide added in step (II).

5. The process as claimed in claim 1, wherein at least a part of the aqueous phase from step (II) is used to neutralize the cleavage products of an acid catalyzed cumene hydroperoxide reaction.

6. The process as claimed in claim 1, wherein the aqueous phase from step (II) contains a metal phenolate and at least a part of the aqueous phase from step (II) is de-phenolated thereby neutralizing the aqueous phase by converting the metal phenolate to a phenol, and then stripping the neutralized aqueous phase with steam in order to remove the phenol from the neutralized aqueous phase.

7. The process as claimed in claim 6, wherein 5 to 30 wt % of the aqueous phase from step (II) is used to neutralize the cleavage products of an acid catalyzed cumene hydroperoxide reaction and 70 to 95% of the aqueous phase from step (II) passes to dephenolation.

8. The process as claimed in claim 1, wherein the concentration of MOH in the aqueous phase in step (II) is about 1 wt %.

9. The process as claimed in claim 1, wherein the concentration of MOH in the second aqueous phase in step (IV) is about 15 wt %.

10. The process as claimed in claim 1, wherein a temperature in at least one of steps (II), (IV) or (VI) is from 30 to 50° C.

11. The process as claimed in claim 1, wherein a pressure in at least one of steps (II), (IV) or (VI) is atmospheric.

12. The process as claimed in claim 1, wherein a temperature in all of steps (II), (IV) and (VI) is from 30 to 50° C.

13. The process as claimed in claim 1, wherein a pressure is atmospheric in all of steps (II), (IV) and (VI).

* * * * *